United States Patent [19]

Osada et al.

[11] Patent Number: 4,570,200
[45] Date of Patent: Feb. 11, 1986

[54] STATIC DISCHARGE DEVICE

[75] Inventors: Masahiko Osada, Hekinan; Akira Kuno, Oubu; Takashi Yamada, Anjo; Sumihiro Kaga, Kariya; Mamoru Shimamoto, Nagoya; Toshitaka Tanahashi, Okazaki, all of Japan

[73] Assignee: Nippondenso Co., Ltd., Tokyo, Japan

[21] Appl. No.: 583,734

[22] Filed: Feb. 27, 1984

[30] Foreign Application Priority Data

Mar. 4, 1983 [JP] Japan ................................. 58-36233

[51] Int. Cl.[4] .............................................. A61N 1/14
[52] U.S. Cl. .................................... 361/212; 361/220; 361/222
[58] Field of Search ...................... 361/212, 220, 222; 174/5 R, 5 SG, 5 SB, 6; D11/61; 40/2 A, 330

[56] References Cited

U.S. PATENT DOCUMENTS

| 3,099,774 | 7/1963 | Crane ................................ 361/220 |
| 3,416,033 | 12/1968 | Hoover et al. ..................... 361/220 |
| 4,349,975 | 9/1982 | Chubb ................................ 40/330 |

FOREIGN PATENT DOCUMENTS 57-58240  9/1980  Japan .

Primary Examiner—Harry E. Moose, Jr.
Attorney, Agent, or Firm—Cushman, Darby & Cushman

[57] ABSTRACT

A static discharge device for preventing an electrostatic shock comprising a conductive body to be grounded to the ground body, a resistance element contacting with the conductive body and having a resistance value to restrict a current value when the conductive body is contact with the ground body by the person, and an insulating material provided between the conductive body and the contacting portion held by the person so as to elongate a creeping distance between the conductive body and the human body.

10 Claims, 13 Drawing Figures

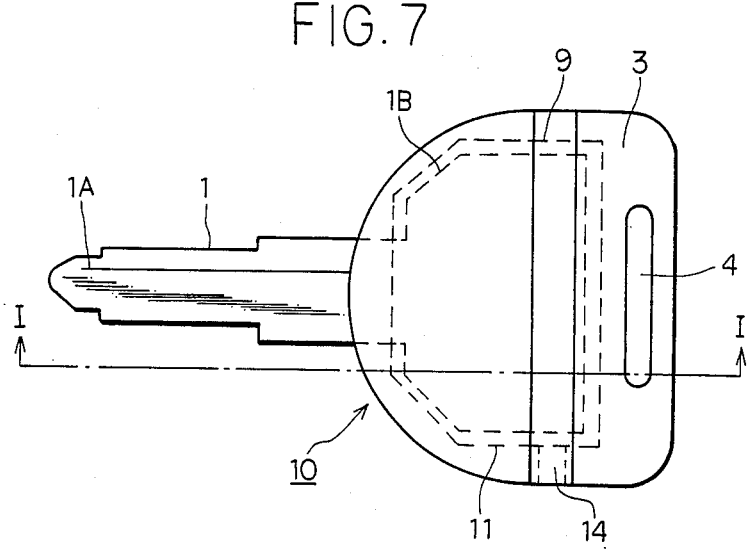
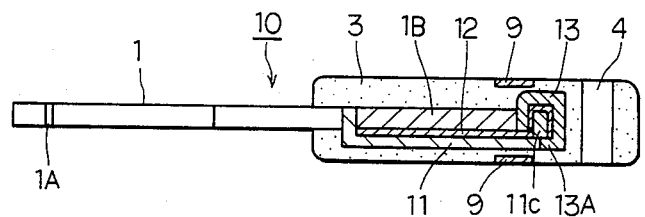
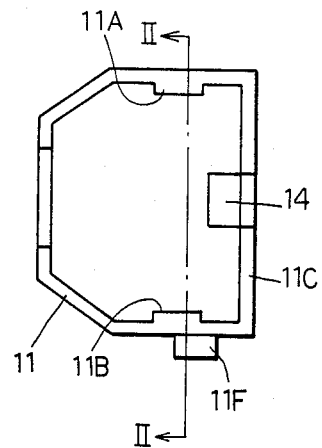
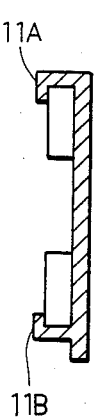
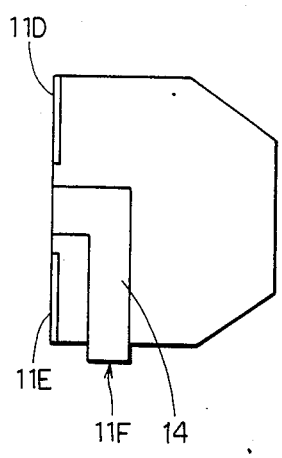

FIG. 12
FIG. 13
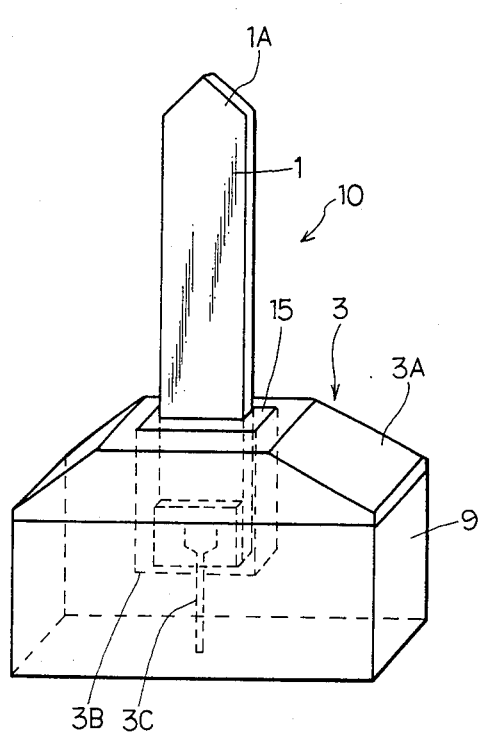

STATIC DISCHARGE DEVICE

BACKGROUND OF THE INVENTION

This invention relates in general to a static discharge device for preventing an electrostatic shock caused when a human body contacts with ground body such as a door-knob. More specifically the present invention provides an automotive vehicle ignition key having an arrangement for minimizing electrostatic discharge shock to a user.

It is well known that when a person leaves a vehicle after driving, he may have been charged with electricity and therefore receive an electrostatic shock when he touches an inside door knob grounded to vehicle chassis.

It was previously proposed to prevent such shock by providing a suitable resistance material between a human body which was a chargeable body and a ground body so that current flow was restricted.

However, according to experiments, it was ascertained that the electrostatic shock which a person feels was not only decided by the magnitude of an electric current flowing through him. Rather it was more painful for him to discharge through a pointed part of his body (for example finger tip) rather than to discharge through a flat part of his body (for example palm). A person feels more pain when the electric discharge energy concentrates on the pointed part, even if the total electric charge is the same.

According to the experiment conducted by the inventors, it became clear that, with respect to a current waveform produced when a person discharges the electric charge generated in his body through a minute air gap, peak value is reduced to a fraction of what it would otherwise be and the electric shock was reduced so much in the case of holding the resistance element having a certain resistance with fingers so as to increase the contacting area relative to the case of touching the ground body with the finger tip.

SUMMARY OF THE INVENTION

It is a major object of this invention to provide a static discharge device which has a resistance element put between a human body and a ground body for restricting an electrostatic shock effectively.

It is a further object of this invention to provide a static discharge device for preventing an electrostatic shock which is small in size and light in weight to be carried by a person and which may be easily utilized and inexpensively manufactured.

With these objects, the static discharge device of the present invention comprises first member to be grounded to a ground body such as an inside door knob of a vehicle, a resistance element having a resistance value required to restrict current value, a second member which includes the resistance element and at which is formed a contacting portion to be contacted with a part of human body, and an insulating member which is provided between the first member and the contacting portion of the second member so as to elongate a distance of creeping discharge between the human body and the first member. Furthermore, the contacting portion of the second member is assured to the extent that density of current flowing through the contacting area should not give the human body the electrostatic shock in cooperation with the resistance element.

BRIEF DESCRIPTION OF THE DRAWINGS

These and other objects and advantages of the invention, as well as the details of an illustrative embodiments, will be more fully understood from the following description and drawings, wherein

FIG. 7 is a plan view showing the structure of a fourth embodiment of the invention;

FIG. 8 is a cross-sectional view taken along the line I—I of FIG. 7;

FIG. 9 is a plan view showing the case of the fourth embodiment of the invention;

FIG. 10 is a cross-sectional view taken along the line II—II of FIG. 9;

FIG. 11 is a bottom view of the case of fourth embodiment of the invention;

FIG. 12 is a perspective view showing the structure of a fifth embodiment of the invention; and FIG. 13 is a perspective view showing a part of the device according to the fifth embodiment.

DETAILED DESCRIPTION OF THE PREFERRED EMBODIMENTS

Figure 1:
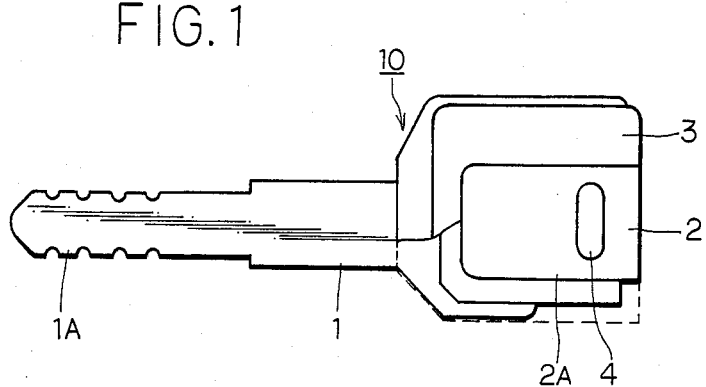
FIG. 1 is a partly broken plan view showing the structure of a first embodiment of the invention.
Figure 2:
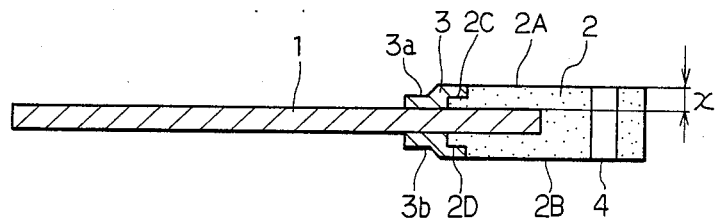
FIG. 2 is a sectional view of FIG. 1.

Referring to the FIG. 1 and FIG. 2, reference numeral 10 refers in general to an automotive vehicle ignition key having a key body 1 made of good conductive material such as brass plated with chrome. Reference numeral 2 is a conductive resin having a resistance value which is controlled by suitably adding 3-12 wt. % carbon to polypropylene in this embodiment. Reference numeral 3 is a stepped insulating resin made of ABS resin. The conductive resin 2 and the insulating resin 3 are molded with the key body 1. In this case, after molding the conductive resin 2 over a portion of the key body 1 flatly, the insulating resin 3 is molded to cover a portion of the key body 1 and stepped portions 2C and 2D of the conductive resin 2.

In this embodiment, the key body 1 is referred to as a first member and has a pointed end 1A which is to be grounded to a ground body such as an inside door knob of the vehicle not shown. The conductive resin 2 is not only a resistance element but also referred to as a second member which has contacting portions 2A and 2B formed to be held by fingers which is a part of a human body. Numeral 4 indicates an opening for a key holder.

Two structural features are significant. The first structural feature is that the insulating resin 3 provided between the contacting portions 2A and 2B of the conductive resin 2 which is contacted with the human body and the key body 1 has stepped portions 3a and 3b. The second structural feature is that step portions 2C and 2D are formed at an end portion of the conductive resin 2 at the side of the key body 1. This structural arrangement effectively elongates a creeping discharge distance between the human body and the key body 1 on the occasion of grounding, and are effective for preventing direct discharge through the air between them.

Further, since the insulating resin 3 is surrounding the stepped external end portion of the conductive resin 2, the key body 1 is prevented from slipping out of the conductive resin 2. As is generally known, in order to enhance the effect of preventing the slipping out a roughness processing such as knurling or opening can be applied to a part of the key body 1 which is inserted into the conductive resin 2.

In the above-described structure of the key, if the thickness of the conductive resin 2 and that of the key body 1 are uniform, and if the carbon is mixed uniformly in the conductive resin 2, the following equation is applicable.

$$R = \rho \cdot (x/s)$$

where
R; a resistance value
S; a contacting area between fingers and the conductive resin 2
$\rho$; resistivity
x; thickness Assuming that the contacting area S is 2.6 (cm$^2$) and that the resistance value is 1 (M$\Omega$), the resistance value R which we need can be obtained by adjusting the resistivity $\rho$ by the rate of carbon contained in the conductive resin 2 and setting the thickness x at the time of molding in relation to the resistivity $\rho$. For example, if the conductive resin 2 is polypropylene and the rate of carbon contained therein is 3–12 wt. %, the thickness can be several millimeters.

Figure 3:
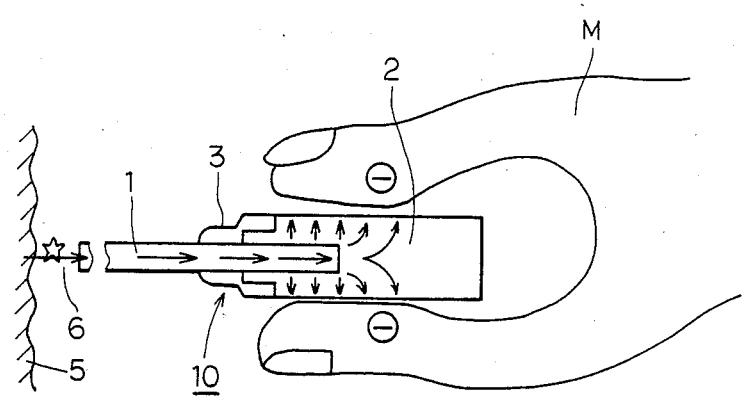
FIG. 3 is a sectional view showing the operation of the device shown in FIG. 1 and FIG. 2.

FIG. 3 illustlates a condition of discharging the electricity in the event that a person M brings the key 10 close to the ground body 5 while he grasps the contacting portions 2A and 2B of the conductive resin 2 between his fingers.

The electric charge generated in the human body M by friction remains in the human body M if the soles of his shoes and the floor are insulated.

The discharge occurs in an air gap 6 at the moment the human body M touches the ground body 5 through the key 10, and then the electric charge so flows as to neutralize the electric charge remaining in the human body M. At this moment, the electric charge flows into the human body M or flows out of the human body M through the key body 1 and the conductive resin 2 as shown by arrows in the FIG. 3.

In this case, as the conductive resin 2 is so formed that the contacting area of fingers is approximately parallel to the metal portion of the key body 1, the current equally flows through the contacting part between the fingers and the contacting portions 2A and 2B so that the current flow area is widened. Consequently the density of current becomes so small that the electrostatic shock is reduced.

Here, if the resistance element which acts to decrease the electric current has a high resistance value at about 1M–10M, the current is apt to discharge in the air rather than to flow in the conductive resin 2, that is, the current begins to discharge to or from the fingers of the human body M directly, when the charged potential becomes high (for example above 10 KV).

In this case, according to the two structural features previously discussed, the creeping distance between the human body M and the key body 1 is elongated so that the electric discharge in the vacant space between the resins 2 and 3 is prevented, and consequently the elimination of the direct electrostatic shock between the human body M and the key body 1 can be effectively achieved.

Figure 4:
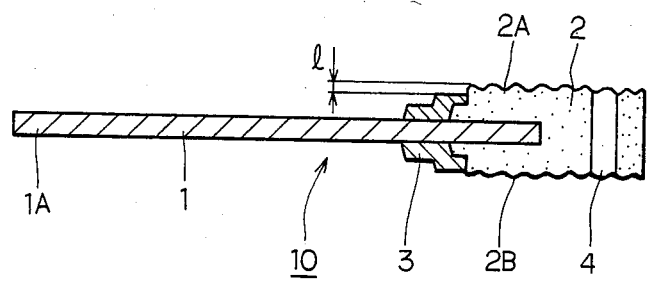
FIG. 4 is a sectional view showing the structure of a second embodiment of the invention.

FIG. 4 shows a second embodiment of the invention which is a partial modification of the first embodiment of this invention described above. In this embodiment, the thickness of the conductive resin 2 is made a little thicker by a distance l than that of the insulating resin 3, so that the fingers can more certainly contact with the contacting portions 2A and 2B of the conductive resin 2 than with the insulating resin 3. Furthermore, as wave-shaped steps which provide minute roughness are formed on the contacting portions 2A and 2B, it is easier to firmly grasp the key 10.

Figure 5:
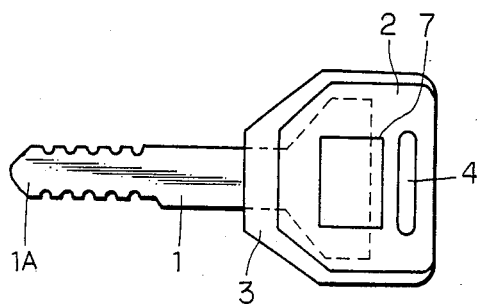
FIG. 5 is a plan view showing the tructure of a third embodiment of the invention.
Figure 6:
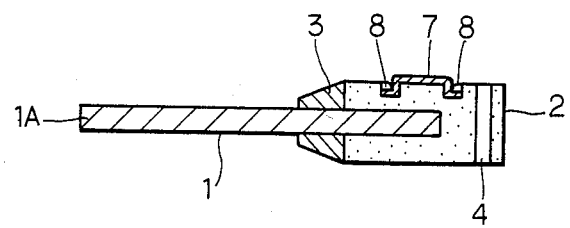
FIG. 6 is a sectional view of FIG. 5.

FIG. 5 and FIG. 6 show the third embodiment of the invention. In order to prevent change of the resistance value due to stain on the surface of the conductive resin 2, a good conductive film 7 is provided on the surface of the conductive resin 2 in contact therewith. This good conductive film 7 can be made of metal plating or secured to the conductive resin 2 by an adhesive agent 8 as indicated in cross section in FIG. 6. It is not to mention that the good conductive film 7 described above can be provided on the surface portion indicated by the reference numerals 2A and 2B in the first embodiment of the invention shown in FIG. 1 and FIG. 2.

As for the first to third embodiments inclusive, the synthetic resin impregnated with carbon as the resistance element is molded integrally with the key body 1 made of metal. But the invention is not to be limited to such as structure.

In this invention, as the resistance element, a film made of conductive high-polymer material such as polyacetylene or polypyrol can be used or a semiconductive ceramic such as $Fe_2O_3$—$SnO_2$, $ZnFe_2$ or $O_4$—$SnO_2$ can be also used.

FIG. 7 and FIG. 8 show a fourth embodiment of the invention in which polyacetylene is used as the resistance element.

On the appearance shown in FIG. 7, the key body 1 is made of a good conductive metal as described above, and a key belly 1B is covered with the insulating resin 3. A plated conductive belt 9 is secured to the insulating resin 3 so as to surround the surface of the insulating resin 3 peripherally. This plated belt 9, forming the contacting portion of the second member to be contacted with the human body, has sufficient surface area for such contact and is spaced from the key body 1 by a sufficient distance.

The key belly 1B is accommodated in a nonconductive case 11 made of resin (for example polypropylene, ABS) as illustrated in FIG. 8.

As shown in FIG. 9 through 11, the case 11 is in a dent shape to accomodate the key belly 1B in the bottom thereof and has nail portions 11A and 11B provided to prevent comming- off of the key belly 1B in the production stage.

When the key body 1 is accomodated in the case 11, a resistance film 12 (resistance element) made of polyacetylene and having a thickness of 0.1–0.2 (mm) is provided between the bottom of the case 11 and the key body 1. Although it is well known that the resistance film 12 can become a conductive TRANS type by applying a heat treatment to a CIS type high purity polyacetylene, the conductivity can be changed if the density of the TRANS type is adjusted by changing the temperature and/or time of the heat treatment.

The resistance film 12 is spread all over the bottom of the case 11 in such a way that one end thereof is pressed and sandwiched between a standing wall 11C provided at the rear end of the case 11 and a nonconductive stopper member 13 shaped into the character C in cross section. The stopper member 13 has two nails 13A and engages with dent portions 11D and 11E provided at one end of the back sole of the case 11.

The electric conduction between the key body 1 and the resistance film 12 is accomplished by contact therebetween. Electric conduction between the resistance film 12 and the plated belt 9 on the outer surface is accomplished in the following way. A projection 11F is integrally formed at the side of the case 11 and a plated conductive belt indicated by reference numeral 14 is provided at the part continuing from the back of the projection 11F to the bottom of the dent of the case 11 so as to connect the belt 9 with the resistance film 12.

As for the production order, the key body 1, case 11, resistance film 12, and stopper member 13 are assembled together first, and then the insulating resin 3 is molded to entirely enclose the assembly therein.

At the time of molding, some measure must be taken so that one end of the plated belt 14 extending to the back of the projection 11F is enabled to expose over the exterior of the insulating resin 3. The plated belt 9 is secured over the insulating resin 3 so that it can keep electric conduction with the exposed portion of the plated belt 14.

The key 10 according to the above-described embodiments in which the resistance film 12 is provided between the human body and the ground body effectively restricts the electrostatic shock as in the first through third embodiments previously described.

FIG. 12 and FIG. 13 show a fifth embodiment in which the insulating resin 3 having an inclined portion 3A is provided with a conductive plated belt 9 thereover. In this case, the outer surface of the insulating resin 3 except the inclined portion 3A is covered with the plated belt 9. Further, the insulating resin 3 is provided with a hole 3B having a flat bottom from which an elongated opening 3C is provided through the insulating resin 3 to the outer bottom surface of the insulating resin 3.

As shown in FIG. 13, a resistance film 12, which is made of polyacetylene as in the fourth embodiment described above, is bent to contact with one end portion of the key body 1. The key body 1 having the resistance film 12 contacting with an electric lead 16 is accommodated in the hole 3B of the insulating resin 3. On the occasion of accommodating them in the hole 3B, a tip 16A of the electric lead 16 reching out of the outer bottom surface of insulating resin 3 through the opening 3C is bent to contact with the plating member 9 and a vacant space around the key body 1, the resistance film 12 and the electric lead 16 is air-tightly filled with the epoxy adhesive resin 15.

The method of use and operational effect in the fifth embodiment are the same as in the previous embodiments.

Of course, the appearence of the key can be freely changed into any shape other than the ones shown in the embodiments described above.

Further, by changing the shape of the key body, it is possible to use it for purposes other than a key, such as for example, a device for preventing electrostatic shock.

Furthermore, a resistor such as for example of the type normally used in electric circuits may be used in place of the conductive resin. In such case, it is necessary to provide the plating or a conductive plate on the outer surface of the case accommodating the resistor.

What is claimed is:

1. A device for preventing electrostatic shock between a human body and a ground body comprising:
   a conductive key body, used for a vehicle ignition switch key, having an exposed portion to be grounded to the ground body;
   a resistance member in contact with said key body at a portion thereof other than said exposed portion and having a predetermined resistance value sufficient to restrict an electric current flowing between said key body and the human body to the extent of not giving the human body an electrostatic shock, said resistance member having a contacting surface sufficiently large to be touched by the human body; and
   an insulating member in contact with said key body and said resistance member structurally arranged so as to elongate a creeping discharge distance between said key body and the human body.

2. A device according to claim 1, wherein said insulating member is provided with a step portion for increasing the distance between the human body and the key body.

3. A device according to claim 1, wherein said insulating member is provided with an inclined portion for increasing the distance between the human body and the key body.

4. A device according to claim 1, wherein said resistance member is formed to provide said contacting surface substantially parallel with a surface of said key body.

5. A device according to claim 1 wherein said resistance member comprises a conductive resin portion in contact wtih said key body and a flat plate over a surface of said conductive resin portion, the flat plate forming said contacting surface.

6. A device according to claim 1, wherein said resistance member includes a resistance film in contact with the key body and a conductive plate provided on an outer surface of said insulating member as said contacting surface and electrically connected with the resistance film.

7. A device for preventing electrostatic shock between a human body and a ground body comprising:
   a conductive key body having a widened belly portion at one end thereof and an exposed pointed portion at the other end opposing said one end to be contacted with the ground body;
   a resistance element provided in contact with and covering the belly portion of said key body and having an exposed flat portion to be contacted with the human body, said resistance element having a resistance value sufficient to restrict between said key body and the human body to the extent of not giving the humam body an electrostatic shock; and
   an insulating member provided in contact with said key body and said resistance element and covering a portion of said key body adjacent to said resistance element so as to elongate a creeping discharge distance between said key body and the human body.

8. A device according to claim 7, wherein said insulating member is formed with a step portion for increasing the distance between the human body and key body.

9. A device according to claim 8, wherein said resistance element is provided with a step portion in contact with and covered by the step portion of said insulating member.

10. An automotive vehicle ignition key having an arrangement for minimizing electrostatic discharge shock to a user comprising:
- an electrically conductive key body having a widened belly portion at one end thereof and an exposed pointed portion at the other end thereof opposing said belly portion end to be contacted with a part of said automotive vehicle;
- a resistance member provided in contact with and covering the belly portion of said key body and having an exposed flat portion substantially parallel with the belly portion of said key body providing a contacting surface to be grasped by the user, said resistance member having a resistance value sufficient to restrict an electric current flow between said key body and the user sufficient to prevent electrostatic shock; and
- an insulating member provided in contact with said key body and said resistance member and having a step portion covering a portion of said key body adjacent to said resistance element for increasing a distance between the user and said key body.

* * * * *